United States Patent [19]

Halazy et al.

[11] Patent Number: 4,988,680

[45] Date of Patent: Jan. 29, 1991

[54] PHOSPHONOALKYLPURINE DERIVATIVES

[75] Inventors: Serge J. Halazy, Wolfisheim; Charles Danzin, Strasbourg, both of France

[73] Assignee: Merrell Dow Pharmaceuticals Inc., Cincinnati, Ohio

[21] Appl. No.: 338,781

[22] Filed: Apr. 14, 1989

[30] Foreign Application Priority Data

Apr. 19, 1988 [EP] European Pat. Off. ........ 88400948.1

[51] Int. Cl.$^5$ .................. A61K 31/675; C07F 9/6524
[52] U.S. Cl. ...................................... 514/81; 544/244; 558/177; 558/188; 558/203; 558/204
[58] Field of Search .......................... 544/244; 514/81

[56] References Cited

U.S. PATENT DOCUMENTS

| | | | |
|---|---|---|---|
| 4,421,767 | 12/1983 | Palfreyman et al. | 560/40 X |
| 4,695,654 | 9/1987 | Gerhart et al. | 564/510 |
| 4,719,313 | 1/1988 | Gerhart et al. | 564/512 |
| 4,730,006 | 3/1988 | Bohme et al. | 514/538 |

FOREIGN PATENT DOCUMENTS 0173624  8/1985  European Pat. Off. .
8404748 12/1984  PCT Int'l Appl. .

OTHER PUBLICATIONS

Davisson et al., Chemical Abstracts, vol. 106: 176792f (1987).
J. M. Stein, Biochemical Pharmacology, vol. 36, No. 8, pp. 1237–1244 (1987).
E. J. Prisbe, et al., *J. Med. Chem.* 29, 671–675 (1986).
C. E. Nakamura et al., Biochemical Pharmacology, vol. 35, No. 2, pp. 133–136 (1986).

*Primary Examiner*—Diana Rivers
*Attorney, Agent, or Firm*—Stephen L. Nesbitt

[57] ABSTRACT

Halogenated 9-phosphonoalkyl derivatives of guanine and hypoxanthine are inhibitors of purine nucleoside phosphorylase and are useful as immuno suppressant and antiparasitic agents as well as against T cell leukemia and antiureicopoietic agents.

31 Claims, No Drawings

PHOSPHONOALKYLPURINE DERIVATIVES

FIELD OF THE INVENTION

This invention relates to certain novel 9-phosphonoalkyl derivatives of purine, the use of these compounds as immunosuppressant, antilymphoma, antileukemic, antiviral, and antiprotozoal agents, pharmaceutical compositions containing these compounds as active ingredients, and the process of their preparation.

BACKGROUND

Purine nucleoside phosphorylase (PNP) under normal *in vivo* conditions catalyzes the phosphorolytic cleavage of the riboand deoxyribonucleosides of guanine and hypoxanthine to the corresponding sugar phosphate and guanine or hypoxanthine. In the absence of PNP, uric acid concentration is quite low while the concentration of certain nucleoside substrates of PNP such as (dGuo) in plasma and urine are elevated. dGuo is toxic towards lymphoblasts, however, T-cells are much more affected than are B-cells. Indeed, in patients with genetically acquired PNP deficiency, B-cell immunoglobulin production is normal or even elevated, but these patients are leukopenic and T-lymphocytic function is either totally lacking or is severely depressed. While uncontrolled PNP deficiency is obviously undesirable, there are many instances where controlled suppression of the immune system, and in particular controlled suppression of T-cells, would be highly desirable such as in the treatment of T-cell leukemia, the supresion of host-vs-graft response in organ transplant recipients, and the treatment of gout. Applicants have discovered a class of phosphonoalkylpurine derivatives which are potent inhibitors of PNP and are thus useful as immunosuppressant agents.

SUMMARY OF THE INVENTION

This invention relates to 9-phosphonoalkylpurines of formula 1:

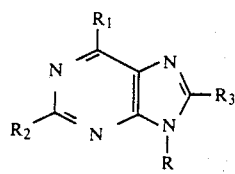

wherein R is a phosphonoalkyl group of the formula:

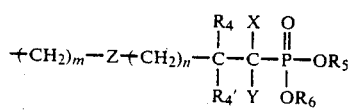

wherein m and n are each an integer of from 1 to 5 with the proviso that m+n must be an integer of from 2 to 6;

Z is an oxy group (—O—) or a methylene group (—CH$_2$—);

R$_4$ is a hydrogen and R$_4'$ is a hydrogen or hydroxy group or R$_4$ and R$_4'$ taken together with the carbon atom to which they are attached form a keto group (C—(O)—);

X and Y are each a hydrogen, fluoro or chloro group with the proviso that both of X and Y cannot be hydrogen;

R$_5$ and R$_6$ are each a hydrogen or a (C-C$_4$)alkyl group;

R$_1$ is a hydroxy or sulfhydryl group;

R$_2$ is a hydrogen or amino (—NH$_2$—) group; and

R$_3$ is a hydrogen, amino (—NH$_2$—), hydroxy or —NH—NH$_2$ group;

or a pharmaceutically acceptable salt thereof are immunosuppresant, antiviral and antiprotozoal agents.

DETAILED DESCRIPTION OF THE INVENTION

The term (C$_1$-C$_4$)alkyl group means a straight or branched alkyl group having from 1 to 4 carbon atoms and includes methyl, ethyl, propyl, isopropyl, sec-butyl, n-butyl, and tert-butyl.

The compounds of this invention are useful both in the free base form and in the form of acid addition salts. The acid addition salts are simply a more convenient form for use and, in practice, use of the salt amounts to use of the free base. The expression "pharmaceutically acceptable acid addition salts" is intended to apply to any non-toxic organic or inorganic acid addition salts of the base compounds of formula 1. Illustrative inorganic acids which form suitable salts include hydrochloric, hydrobromic, sulfuric, and phosphoric acids and acid metal salts such as sodium monohydrogen orthophosphate and potassium hydrogen sulfate. Illustrative organic acids which form suitable salts include the mono, di, and tricarboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic, and 2-phenoxybenzoic acids. Other organic acids which form suitable salts are the sulfonic acids such as methane sulfonic acid and 2-hydroxyethane sulfonic acid. Either the mono- or the di-acid salts can be formed, and such salts can exist in either a hydrated or a substantially anhydrous form. The acid salts are prepared by standard techniques such as by dissolving the free base in aqueous or aqueous-alcohol solution or other suitable solvent containing the appropriate acid and isolating by evaporating the solution, or by reacting the free base in an organic solvent in which case the salt separates directly or can be obtained by concentration of the solution. In general the acid addition salts of the compounds of this invention are crystalline materials which are soluble in water and various hydrophilic organic solvents and which in comparison to their free base forms, demonstrate higher melting points and an increased stability.

As should be apparent, the compounds of this invention are hypoxanthine, 6-mercaptopurine, guanine, and 6-thioguanine derivatives. Those compounds of formula 1 wherein R$_2$ is a hydrogen are hypoxanthine derivatives and those compounds of formula 1 wherein R$_2$ is a —NH$_2$ group are guanine derivatives. The guanine derivatives are preferred. Also preferred are those compounds of formula 1 wherein one or both of R$_5$ and R$_6$ are hydrogen, that is the free phosphonic acid derivatives. Those compounds wherein both of R$_5$ and R$_6$ are hydrogen are especially preferred. Also preferred are those compounds wherein R$_4$ and R$_4'$ are each a hydrogen. Also preferred are those compounds of formula 1 wherein one or both of X and Y are a fluoro group. Those compounds wherein X and Y are both fluoro groups are especially preferred. Also preferred are those compounds of formula 1 wherein $R_3$ is a hydrogen or an amino group. Finally those compounds wherein Z is a methylene group and $m+n = 2, 3, 4$ and 5 are preferred with the $m+n = 2$ compounds being especially preferred. Representative compounds of this invention are:

9-(7-phosphono-7,7-difluoroheptyl)hypoxanthine;
9-(7-phosphono-7,7-difluoroheptyl)guanine;
8-amino-9-(7-phosphono-7,7-difluoroheptyl)-guanine;
8-hydroxy-9-(7-phosphono-7,7-difluoroheptyl)-guanine;
9-(7-phosphono-7,7-difluorohept-6-ol)guanine;
8-amino-9-(7-phosphono-7,7-difluorohept-6-ol)-guanine;
8-amino-9-(6-phosphono-5,5-difluorohexyl)guanine;
8-amino-9-(7-phosphono-7-fluoroheptyl)guanine;
6-mercapto-9-(7-phosphono-7,7-difluoroheptyl)-guanine;
9-[(3,3-difluoro-3-phosphonopropoxy)methyl]-guanine;
8-amino-9-[(3,3-difluoro-3-phosphonopropoxy)methyl]guanine;
9-[(5,5-difluoro-5-phosphonopentoxy)methyl]guanine;
8-amino-9-[(5,5-difluoro-5-phosphonopentoxy)methyl]guanine;
6-mercapto-9-[(3,3-difluoro-3-phosphonopropoxy)methyl]guanine;
8-amino-[9-(5-phosphono-5,5-difluoropentyl)]guanine; and
8-amino-[9-(5-phosphono-5,5-difluoropentyl)guanine].

The compounds of formula 1 wherein R, $R_2$, m, n, X, Y, and Z are as defined for formula 1 and wherein $R_4$ is a hydrogen, $R_4'$ is a hydrogen or a methyloxymethyleneoxy group, $R_5$ and $R_6$ are other than hydrogen, $R_1$ is a hydroxy group, and $R_3$ is a hydrogen may be prepared by the condensation of a purine derivative of formula 2 wherein $R_2$ is a hydrogen or amino group with an appropriate phosphonoalkylhalide, preferably a phosphonoalkylbromide or iodide (RBr or RI) to yield an intermediate of formula 3 which upon acid catalyzed hydrolysis gives the desired compound according to as shown below.

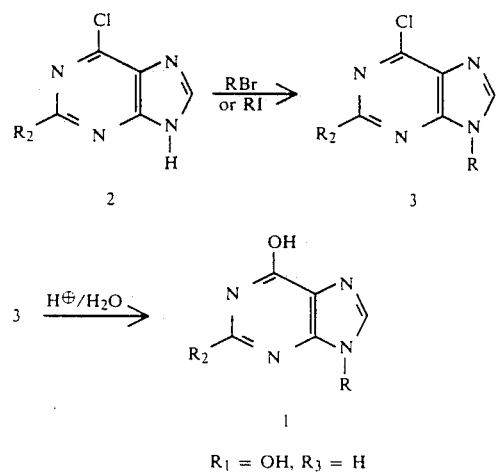

$R_1 = OH, R_3 = H$

The condensation reaction can be performed by, for example, adding a mild base such as potassium carbonate to a solution of the appropriate formula 2 compound and the appropriate phosphonoalkylbromide (RBr) and allowing the mixture to react until product formation is complete. While a 1:1 molar ratio of the formula 2 compound and the phosphonoalkylbromide can be used, it is preferable to use a slight molar excess of the formula 2 purine derivative such as a 10 per cent molar excess. The solvent can be any suitable solvent which does not interfere with the reaction, but a solvent known to promote nucleophilic reactions is preferred. Such solvents include preferably dimethylformamide (DMF). The base acts as a catalyst and any amount of base sufficient to speed up the reaction can be used. Applicants have found that from about 1 to about 5, preferably about 2 molar equivalents of the base is suitable. Any convenient temperature can be employed, for example, from 0° C. to 60° C., preferably about room temperature, i.e., from 20° C. to 30 ° C. The time of the reaction varies with the reactants and other conditions but is typically from about 4 to about 18 hours, preferably about 8 to 10 hours. The product can be isolated from the reaction mixture in any suitable manner such as by evaporating the solvent, washing the resulting residue with a solvent, for example, ethyl acetate, and removing the ethyl acetate by evaporation.

The hydrolysis reaction can be carried out by, for example, reacting the appropriate formula 3 compound with formic acid (1N) at from 80°–100° C. for from about 1 to about 12 hours. This reaction will transform, not only the chloro group at the 6-position of the purine nucleus to an hydroxy group, but where the $R_4'$ is a methyloxymethyleneoxy group it will be transformed to an hydroxy group as well. To prepare those compounds wherein $R_4'$ is a hydroxy, the corresponding compound wherein $R_4'$ a methyloxymethyleneoxy group is prepared and then subjected to acid hydrolysis, for example, by reaction with formic acid at from 80°–100° C. for from about 1 to about 12 hours.

To prepare those compounds of formula 1 wherein $R_2$, m, n, X, Y, and Z are as defined for formula 1 and wherein $R_5$ and $R_6$ are other than hydrogen, $R_1$ is an hydroxy group, $R_3$ is a hydrogen, and wherein $R_4$ and $R_4'$ taken together with the carbon atom to which they are attached form a keto group, the appropriate hydrolysis product wherein $R_4'$ is hydroxy is subjected to a Swern oxidation, a well known procedure for transforming an alcohol into an aldehyde or ketone. The Swern oxidation is preformed by treating the reactant alcohol with dimethylsulfoxide and an acid halide or anhydride such as oxalyl chloride.

To prepare those compounds of formula 1 wherein $R_1$ is an hydroxy group and wherein both $R_5$ and $R_6$ are a hydrogen, the corresponding compounds wherein $R_1$ is a chlorine atom and wherein $R_5$ and $R_6$ are a $(C_1-C_4)$alkyl group (preferably an ethyl) are successively reacted with trimethylsilylbromide (TMSBr) in $CH_2Cl_2$, water in acetonitrile (to get the compounds in which $R_1 = Cl$ and $R_5 = R_6 = H$)3 and finally in HCl(1N) at 90° C.

To prepare those compounds of formula 1 wherein $R_1$ is an hydroxyl group and wherein $R_5$ is an hydrogen and $R_6$ is a $(C_1-C_4)$alkyl group, the corresponding compounds of formula 1 wherein $R_1$ is Cl and wherein both $R_5$ and $R_6$ are a $(C_1-C_4)$alkyl group are submitted directly to HCl/$H_2O$ hydrolysis at 90° C.

To prepare those compounds of formula 1 in which $R_1 = SH$ and $R_5$ and $R_6$ are both hydrogen atoms, the corresponding compounds in which $R_1=SH$ and $R_5$ or $R_6$ are both a $(C_1-C_4)$alkyl group are reacted with TMSBr and hydrolyzed.

The compounds of formula 1 wherein R, $R_2$, $R_4$, $R_4'$ m, n, X, Y, and Z are as defined for formula 1, $R_1$ is a sulfhydryl group, $R_3$ is a hydrogen, and $R_5$ and $R_6$ are each other than hydrogen can be obtained by reacting the appropriate compound of formula 3 wherein the definitions of the groups are the same as described above for formula 3 with thiourea in acetic acid as shown below.

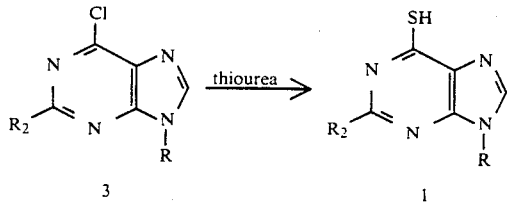

To prepare those compounds wherein $R_4'$ is a hydroxy, as described above the corresponding compound wherein $R_4'$ a methyloxymethyleneoxy group is prepared and then subjected to acid hydrolysis, for example, by reaction with formic acid (1N) at from 80°–100° C. for from about 1 to about 12 hours. To prepare those compounds wherein $R_4$ and $R_4'$ taken together with the carbon atom to which they are attached form a keto group, as described above the appropriate hydrolysis product wherein $R_4'$ is a hydroxy group is subjected to a Swern oxidation, that is by treating the reactant with dimethylsulfoxide and an acid anhydride such as trifluoroacetic acid anhydride.

The compounds of formula 1 wherein $R_3$ is other than hydrogen are prepared from an appropriate compound of formula 4 wherein R, $R_2$, m, n, $R_5$, $R_6$, X, Y, and Z are as defined for formula 1 and wherein $R_4$ is a hydrogen and $R_4'$ is a hydrogen or a methyloxymethyleneoxy group. As illustrated below, the formula 4 compounds are in turn prepared from a corresponding compound of formula 3 by halogenation preferably using a brominating or iodinating agent such as bromine in water, a N-bromo or N-iodoimide, for example, 1,3-dibromo-5,5-dimethylhydantoin, 1,3-diiodo-5,5-dimethylhydantoin, N-iodoacetamide, N-bromosuccinimide or preferably N-iodosuccinimide or more preferably N-bromoacetamide (NBA).

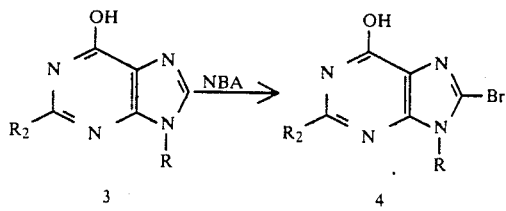

To prepare those compounds of formula 1 wherein $R_3$ is a -NHNH$_2$ group, the appropriate formula 4 compound is reacted with hydrazine. Typically this reaction would be performed in a solvent, for example, an ethereal solvent such as water, diethyl ether, tetrahydrofuran (THF) or p-dioxan, an alcoholic solvent such as ethanol, isopropanol, methanol, t-butanol, or ethylene glycol, a chlorinated hydrocarbon solvent such as dichloromethane, chloroform, or ethylene dichloride, or one of the polar, aprotic solvents known to promote substitution reactions such as dimethylformamide (DMF), hexamethylphosphoramide (HMPA), or dimethylsulfoxide (DMSO). Although only a stoichiometric amount of hydrazine is required it is preferable to employ a two or three fold excess of this reagent. Although this reaction may conveniently be carried out at room temperature, elevated temperatures such as from 50° to 100° C. promote the rate of this reaction. When complete the product can be isolated from the reaction mixture and purified in any suitable manner generally known to those skilled in the art.

To prepare those compounds wherein $R_3$ is an NH$_2$ group, an appropriate compound in which $R_3$ is a NHNH$_2$ group is reduced preferably by using Raney Nickel.

In order to prepare those compounds of formula 1 wherein $R_3$ is a hydroxy group, the appropriate compound of formula 4 is reacted with an alkali metal or alkaline earth metal salt, preferably a sodium salt, of a benzyl alcohol such as benzyl alcohol. Subsequent reduction of the intermediate compound with hydrogen gas at atmospheric pressure in the presence of a noble metal catalyst such as a palladium on carbon catalyst results in the desired alcohol derivative.

The compounds of formula 1 wherein $R_1$ is a sulfhydryl group and wherein $R_4'$ is hydrogen or a hydroxyl group can be prepared by the reaction of dimeric phosphorus pentasulfide with the corresponding compounds of formula 1 wherein $R_1$ is a hydroxyl group as shown below:

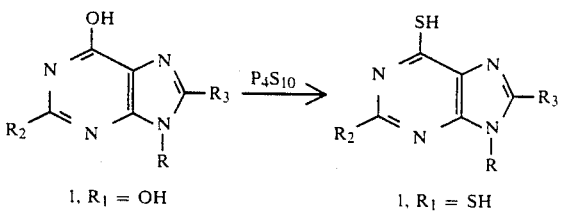

This reaction is well known and can be performed in a manner analogous to that described in *J. Amer. Chem. Soc.* 80, 6671 (1958). To prepare the compounds of formula 1 wherein $R_1$ is a sulfhydryl group and $R_4'$ is other than hydrogen or a hydroxyl group, the resultant compound is subjected to a Swern oxidation.

The phosphonoalkylbromides (RBr) and the phosphonoalkyliodides (RI) of formula 5 in which Z =CH$_2$, $R_4$ and $R_4$=H, X and Y=F and $R_5$ and $R_6$=ethyl are prepared by reacting excess symmetrical dibromo or diiodo alkane with reagent 6 (X and Y=F, $R_5$ and $R_6$=ethyl) in THF or ether at −78° C.

The phosphonoalkylbromides (RBr) of formula 5

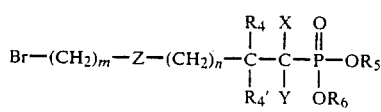

wherein m, n, X, Y, Z, $R_5$, and $R_6$ are as defined above for formula 1 except that $R_5$ and $R_6$ are other than a hydrogen and $R_4$ is a hydrogen and $R_4'$ is a hydrogen or a methyloxymethyleneoxy group (—OCH$_2$OCH$_3$) are readily prepared by techniques generally known to those skilled in the art. The compounds of formula 1 wherein $R_5$ and $R_6$ are hydrogens are prepared using the corresponding phosphonoalkylbromides wherein $R_5$ and $R_6$ are other than hydrogens and the compounds of formula 1 wherein $R_4'$ is a hydroxy group or wherein $R_4$ and $R_4'$ taken together with the carbon atom to which they are attached form a keto group are prepared using the corresponding phosphonoalkylbromide wherein $R_4'$ is —OCH$_2$OCH$_3$. The phosphonoalkylbromides of formula 5 wherein Z is a methylene group and $R_4$ and $R_4'$ are each a hydrogen, can be prepared by low temperature reaction of a lithiated anion of formula 6

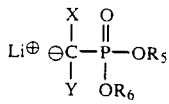
                                  6 with an appropriate benzyloxyalkyliodide of formula 7

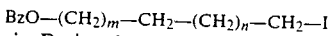
                                  7 wherein Bz is a benzyl group. These reactions are performed by the dropwise addition of a solution of about one molar equivalent the benzyloxyalkyliodide in, for example, tetrahydrofuran (THF), diethyl ether, or a mixture of THF and diethyl ether, to a stirred solution of the anion generally prepared *in situ* by the procedure reported in Synthesis 615 (1977) and maintained at from about −78° C. to about −90° C. The chlorofluoromethanephosphonate is known from this Synthesis article and the difluorolithiomethane phosphate has been described in *Tetrahedron Letters*, 2323 (1982). After several hours, generally from about 1 to 5 hours, the reaction mixture is allowed to warm to about room temperature and is then quenched with aqueous ammonium chloride. After solvent removal, the intermediate product of formula 8

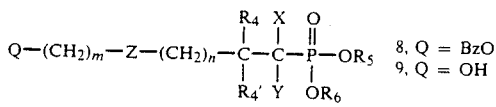

wherein Z is a methylene group and $R_4$ and $R_4'$ are both hydrogens is extracted into ethylacetate and can be purified by, for example, flash chromatography. The alcohol derivative of formula 9 is then prepared by catalytic hydrogenation using, for example, platinum, platinum oxide, rhodium, ruthenium, or preferably palladium on carbon, in the usual manner and the resulting hydroxy group is converted to a bromine group by, for example, reaction with molecular bromine and triphenylphosphine to give the desired phosphonoalkylbromide of formula 5.

The phosphonoalkylbromides of formula 5 wherein Z is a methylene group, $R_4$ is a hydrogen, $R_4'$ is a methyloxymethyleneoxy group, can be prepared in a manner analogous to that described above by low temperature reaction of a lithiated anion of formula 6 with a benzyloxyaldehyde of formula 10.

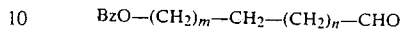

The resulting intermediate compound of formula 11

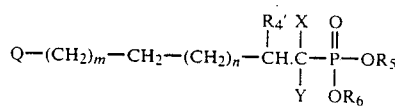

11, $R_4'$ = OH, Q = BzO;
12, $R_4'$ = OCH$_2$OCH$_3$
    Q = BzO;
13, $R_4'$ = OCH$_2$OCH$_3$
    Q = OH is then converted into the methyloxymethyleneoxy derivative of formula 12 by the acid catalyzed reaction with dimethoxymethane. This reaction is well known to those skilled in the art and is commonly employed as a means of protecting or masking alcohols. Preferably the acid catalyst will be diphosphoruspentoxide and preferably an excess of dimethoxymethane will be employed. The intermediate compound of formula 12 is then converted into the desired phosphonoalkylbromide via the compound of formula 13 by catalytic hydrogenation and subsequent conversion of the resulting hydroxy group into a bromine group in a manner analogous to that described above.

The phosphonoalkylbromides of formula 5 wherein Z is an oxygen group and m is other than 1 can be prepared as illustrated below by treating an omega benzyloxyalcohol of formula 14 with about 1 equivalent of sodium hydride and subsequently treating the resulting alcoholate with a dibromide of formula 15a or a bromo aldehyde of formula 15b to form the intermediate benzyloxyalkyloxy derivative of formula 16a or 16b as appropriate. The formula 16a or 16b compound is then treated with a lithiated anion of formula 6 to give a compound of formula 8 wherein Z is an oxy group, $R_4$ is a hydrogen and $R_4'$ is a hydrogen or hydroxy group.

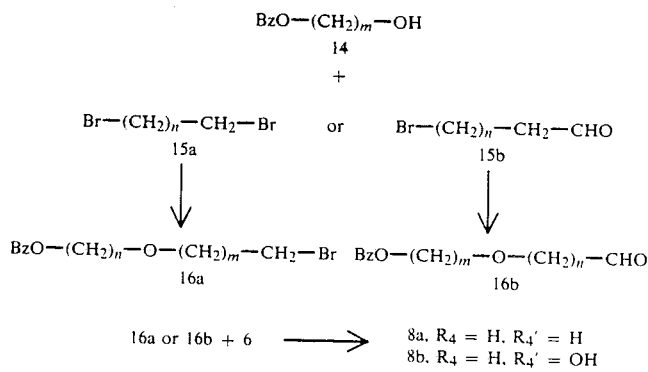

The formula 8b alcohol is then converted to its methyloxymethyleneoxy derivative and these formula 8 compounds are converted to the desired formula 5 compounds as described above.

The ability of the compounds of this invention to act as immunosuppressant antilymphoma, antileukemic, antiviral, and antiprotozoal agents can be demonstrated by their ability to inhibit purine nucleoside phosphorylase (PNP). Purine nucleoside phophorylase (PNP) inhibitory activity can be determined by the coupled xanthine oxidase method of Kalckar, using inosine as the substrate (H. M. Kalckar, *J. Biol. Chem.* 167, 429-443 (1974)). Apparent dissociation constants ($K_I$) were measured at 1 mM inorganic phosphate using 0.1M HEPES buffer (pH 7.4), four concentrations of inosine ranging from 0.05 mM to 0.15 mM and various concentrations of inhibitor. The $K_i$ for representative members of the compounds of formula 1 are tabulated in table 1 and are compared to the $K_M$ values of the substrate inosine using PNP from various sources. Moreover, compounds of this invention have been shown to be effective against lymphomas (human MoLT cells) and thus are antilymphomic, antileukemic immunodulators. The presence of 2'-deoxyguanosine (about 10 μM), a natural metabolite, appears to be important in *in vitro* activity.

| COMPOUND | $K_i$ (M) PNP SOURCE | | |
|---|---|---|---|
| | Calf Spleen | Rat Erythrocytes | Human Erythrocytes |
| 9-(7-phosphono-7,7-difluoroheptyl)hypoxanthine | $2.2 \times 10^{-6}$ | $1.6 \times 10^{-7}$ | $1 \times 10^{-7}$ |
| 9-(7-phosphono-7,7-difluoroheptyl)guanine | $1.5 \times 10^{-7}$ | $9.6 \times 10^{-9}$ | $8 \times 10^{-8}$ |
| 9-(7-phosphono-heptyl)guanine | $1.2 \times 10^{-6}$ | $7.5 \times 10^{-8}$ | $6.8 \times 10^{-7}$ |
| 9-(6-phosphono-6,6-difluorohexyl)guanine | $3.2 \times 10^{-7}$ | $1.8 \times 10^{-7}$ | $2.8 \times 10^{-7}$ |
| 9-(8-phosphono-8,8-difluorooctyl)guanine | $6.2 \times 10^{-7}$ | $4.6 \times 10^{-9}$ | $1.9 \times 10^{-7}$ |
| 9-(7-phosphono-7,7-difluoroheptyl)guanine, ethyl ester | $3.3 \times 10^{-6}$ | $2.8 \times 10^{-7}$ | $8 \times 10^{-7}$ |
| 9-(5-phosphono-5,5-difluoropentyl)guanine | $1.6 \times 10^{-8}$ | $3.5 \times 10^{-8}$ | $1.5 \times 10^{-8}$ |
| inosine | $28 \times 10^{-6}$ | $80 \times 10^{-6}$ | $70 \times 10^{-6}$ |

As used herein the term patient in regard to the suppression of immune system means mammals such as mice, rats, cats, dogs, cattle, sheep, swine, and primates including humans. The term patient in regard to the treatment of parasitic infections includes not only mammals but also other warm blooded animals such as fowl including chickens and turkeys.

The term protozoa is intended to include those members of the subphyla *Sarcomastigophora* and *Sprozoa* of the phylum *Protozoa*. More particularly the term protozoa as used herein is intended to include those genera of parasitic protozoa which are important to man because they either cause disease in man or in his domestic animals. These genera are for the most part found classified in the superclass of *Mastigophora* of the subphylum *Sarcomastigophora* and the class of *Telosporea* the subphylum *Sporozoa* in the classification according to Baker (1969). Illustrative genera of these parasitic protozoa include *Histomonas, Trypanosoma, Giardia, Trichomonas, Eimeria, Isopora, Toxoplasma,* and *Plasmodium*.

Indeed, a preferred embodiment of the present invention is the use of these compounds as antiprotozoal agents in the treatment of intestinal coccidia in commercial poultry. Intestinal coccidia infections are responsible for multimillion dollars loses to the poultry industry in the United States each year. Due to the rapid development of drug resistance by coccidia, and due to the relatively high toxicity of some of the drugs used in the treatment of coccidiosis, there is a need for effective coccidiostats that are non-toxic and to which intestinal coccidia do not develop rapid drug resistance.

Although the immune system is a major defense against substances which can cause disease, it cannot distinguish between helpful and harmful foreign substances and destroys both. It would be useful in many instances to have a means of regulating the immune system without harming the individual. The compounds of this invention exhibit such modulating or regulatory effects and have potential for use in the treatment of various immune disorders.

Circulating antibodies and cellular immune responses play a role in the rejection of transplanted tissues and organs. Unless the donor is the identical twin of the recipient or is the individual himself, the recipient's lymphocytes recognize the transplant as "not self" and immediately respond to destroy it. The exceptions to this situation are transplants to non-vascularized areas (privileged sites), such as the cornea of the eye, where lymphocytes do not circulate and therefore are not sensitized and do not prompt an immune response. It is currently difficult to suppress the immune reaction to prevent rejection of the transplant without severely damaging the patient in other ways. The patient must also be given massive doses of antibiotics because his own defenses against infection have been suppressed. The compounds of this invention could be valuable in establishing tolerance to the transplant through controlled modulation of the immune system. In addition, these compounds demonstrate antiviral activities.

The amount of the active ingredient to be administered can vary widely according to the particular dosage unit employed, the period of treatment, the age and sex of the patient treated and the nature and extent of the disorder treated. The total amount of the active ingredient to be administered will generally range from about 1 mg/kg to 100 mg/kg and preferably from 3 mg/kg to 25 mg/kg. A unit dosage may contain from 25 to 500 mg of active ingredient, and can be taken one or more times per day. The active compound of formula 1 can be administered with a pharmaceutical carrier using conventional dosage unit forms either orally, parenterally, or topically. In a preferred mode, 2-deoxyguanosine will be administered conjunctively with a compound of this invention. Any effective nontoxic dose of 2-deoxyguanosine can be used, typically from about 0.5 to about 50 mg/kg per day will be administered. By conjunctively applicants contemplate not only those dosage forms which contain both 2-deoxyguanosine and a compound of formula 1, but also separate dosage forms. the compounds may also be administered in separate dosage units.

The preferred route of administration is oral administration. For oral administration the compounds can be formulated into solid or liquid preparations such as capsules, pills, tablets, troches, lozenges, melts, powders, solutions, suspensions, or emulsions. The solid unit dosage forms can be a capsule which can be of the ordinary hard- or soft-shelled gelatin type containing, for example, surfactants, lubricants, and inert fillers such as lactose, sucrose, calcium phosphate, and cornstarch. In another embodiment the compounds of this invention can be tableted with conventional tablet bases such as lactose, sucrose, and cornstarch in combination with binders such as acacia, cornstarch, or gelatin, disintegrating agents intented to assist the break-up and dissolution of the tablet following administration such as potato starch, alginic acid, corn starch, and guar gum, lubricants intented to improve the flow of tablet granulations and to prevent the adhesion of tablet material to the surfaces of the tablet dies and punches, for example, talc, stearic acid, or magnesium, calcium, or zinc stearate, dyes, coloring agents, and flavoring agents intented to enhance the aesthetic qualities of the tablets and make them more acceptable to the patient. Suitable excipients for use in oral liquid dosage forms include diluents such as water and alcohols, for example, ethanol, benzyl alcohol, and the polyethylene alcohols, either with or without the addition of a pharmaceutically acceptably surfactant, suspending agent, or emulsifying agent.

The compounds of this invention may also be administered parenterally, that is, subcutaneously, intravenously, intramuscularly, or interperitoneally, as injectable dosages of the compound in a physiologically acceptable diluent with a pharmaceutical carrier which can be a sterile liquid or mixture of liquids such as water, saline, aqueous dextrose and related sugar solutions, an alcohol such as ethanol, isopropanol, or hexadecyl alcohol, glycols such as propylene glycol or polyethylene glycol, glycerol ketals such as 2,2-dimethyl-1,3-dioxolane-4-methanol, ethers such as poly(ethyleneglycol) 400, an oil, a fatty acid, a fatty acid ester or glyceride, or an acetylated fatty acid glyceride with or without the addition of a pharmaceutically acceptable surfactant such as a soap or a detergent, suspending agent such as pectin, carbomers, methylcellulose, hydroxypropylmethylcellulose, or carboxymethylcellulose, or emulsifying agent and other pharmaceutical adjuvants. Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum, and mineral oil. Suitable fatty acids include oleic acid, stearic acid, and isostearic acid. Suitable fatty acid esters are, for example, ethyl oleate and isopropyl myristate. Suitable soaps include fatty alkali metal, ammonium, and triethanolamine salts and suitable detergents include cationic detergents, for example, dimethyl dialkyl ammonium halides, alkyl pyridinium halides, and alkylamines acetates; anionic detergents, for example, alkyl, aryl, and olefin sulfonates, alkyl, olefin, ether, and monoglyceride sulfates, and sulfosuccinates; nonionic detergents, for example, fatty amine oxides, fatty acid alkanolamides, and polyoxyethylenepolypropylene copolymers; and amphoteric detergents, for example, alkyl-beta-aminopropionates, and 2-alkylimidazoline quarternary ammonium salts, as well as mixtures. The parenteral compositions of this invention will typically contain from about 0.5 to about 25% by weight of the active ingredient in solution. Preservatives and buffers may also be used advantageously. In order to minimize or eliminate irritation at the site of injection, such compositions may contain a non-ionic surfactant having a hydrophile-lipophile balance (HLB) of from about 12 to about 17. The quantity of surfactant in such formulations ranges from about 5 to about 15% by weight. The surfactant can be a single component having the above HLB or can be a mixture of two or more components having the desired HLB. Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

Aerosol or spray compositions containing the compounds of this invention can be applied to the skin or mucous membranes. Such compositions may contain a micronized solid or a solution of a compound of formula 1 and may also contain solvents, buffers, surfactants, perfumes, antimicrobial agents, antioxidants, and propellants. Such compositions may be applied by means of a propellant under pressure or may be applied by means of a compressible plastic spray bottle, a nebulizer, or an atomizer without the use of a gaseous propellant. A preferred aerosol or spray composition is a nasal spray.

The active ingredient may also be administered by means of a sustained release system whereby the compound of formula 1 is gradually released at a controlled, uniform rate form an inert or bioerodible carrier by means of diffusion, osmosis, or disintegration of the carrier during the treatment period. Controlled release drug delivery systems may be in the form of a patch or bandage applied to the skin or to the buccal, sublingual, or intranasal membranes, an ocular insert placed in the cul de sac of the eye, or a gradually eroding tablet or capsule or a gastrointestinal reservoir administered orally. Administration by means of such sustained release delivery systems permits the tissues of the body to be exposed constantly for a prolonged time period to a therapeutically or prophylactically effective dosage of a compound of formula 1. The unit dosage of the compound administered by means of a sustained release system will approximate the amount of an effective daily dosage multiplied by the maximun number of days during which the carrier is to remains on or in the body of the host. The sustained release carrier may be in the form of a solid or porous matrix or reservoir and may be formed from one or more natural or synthetic polymers, including modified or unmodified cellulose, starch, gelatin, collagen, rubber, polyolefins, polyamides, polyacrylates, polyalcohols, polyethers, polyesters, polyurethanes, polysulphones, polysiloxanes, and polyimides as wells as mixtures and copolymers of these polymers. The compounds of formula 1 may be incorporated in the sustained release carrier in a pure form or may be dissolved in any suitable liquid or solid vehicle, including the polymer of which the sustained release carrier is formed.

EXAMPLES

The following nonlimiting examples are intended to illustrate the preparation and use of the compounds of this invention.

EXAMPLE 1

Preparation of
9-(7-phosphinyl-7,7-difluoroheptyl)guanine

A. Synthesis of (Diethyl phosphinyl)difluoromethane 17.3 g of NaH (360 mmoles of a 50% suspension in oil) are introduced in a 1 liter three necked flask (equipped with a reflux condenser and connected to a stream of argon) and washed 3 times with 30 cc of anhydrous hexane using a syringe. When all the hexane is removed, the remaining solid is suspended in 500 ml of dried THF. Diethylphosphonate (50 g) dissolved in 100 ml of THF is then added to the stirred suspension. Addition must be slow as a vigorous exothermic reaction takes place ($H_2$ evol. is observed). The reaction is then stirred at 20° C. for 30 minutes, cooled at 0° C., and a stream of chlorodifluoromethane ($CHClF_2$) is bubbled into the reaction mixture during 1 hour (the orange solution turns to a white suspension). Stirring at 20° C. is continued overnight. The reaction is quenched by the addition of 100 ml of water, evaporation of THF, extraction with ether (3×). The organic layers are gathered, washed with brine, dried over sodium sulfate, filtrated and evaporated. The residue is distilled (84° C./1mmHg) giving 42.95 g of product (64%).

B. Synthesis of 1-O-Benzyl-7,7-difluoro-7-(diethylphosphinyl)heptane 76.6 ml of n-butyllithium (82 mmoles of a 1.07M in hexane) are added to a stirred solution of 12 ml (86 mmoles) of diisopropylamine dissolved in 90 ml of anhydrous THF at 0° C. under argon; stirring at 0° C. for 30–40 minutes. This solution is cooled to −78° C. and slowly added to a solution of (diethylphosphono)difluoromethane (15.43 g, 82 mmoles) dissolved in 90 ml of THF at −78° C. under argon. When addition is complete (±15 min), the solution is stirred for another 5 min at −78° C. and 6-bromo-1-benzyloxyhexane (45.5 mmoles, 12.35 g) dissolved in 90 ml of THF is added to the reaction mixture. Stirring is continued for 2 hours at −78° C. and a few minutes at 20° C. The brown solution is quenched with saturated aqueous ammonium chloride, evaporated, and extracted with ethylacetate. The organic layers are gathered, washed with $HN_4Cl$, brine, dried over $Na_2SO_4$, filtered, and evaporated. The crude product (23.65 g) is purified by flash chromatography.

TLC:Rf==0.35 (hexane/EtOAc-75/25)
sprayed with $MoO_3/H_2SO_4$; visible in UV
6.91 g of product, 40%

C. Synthesis of 7,7-difluoro-7-(diethyl phosphinyl)-heptane-1-ol 11.25 g of 1-O-benzyl-7,7-difluoro-7-(diethylphosphono)heptane (30 mmoles) are dissolved in 100 ml of THF and hydrogenated in the presence of 1.5 g of Pd/C overnight (700 ml of $H_2$ are consumed). Filtration over celite, washing with THF, and evaporation give 8.17 g of product pure as indicated by TLC (hex-/EtOAc=60/40, Rf=0.15) and NMR. This product is used without purification in the next step.

D. Synthesis of 1-bromo-7,7-difluoro-7-(diethylphosphinyl)heptane 28 mmoles of bromine (4.5 g) dissolved in 30 ml of benzene are added (1 hour) to a stirred solution of triphenyl phosphine (7.8 g, 30 mmoles) in 120 ml of benzene at 0° C. under nitrogen. The yellow solution is then successively treated (0° C.) by 3.9 ml (29 mmoles) of triethylamine and 7.7 g (26.8 mmoles) of the product of part C dissolved in 5 ml of benzene. Stirring at 20° C. overnight. The reaction mixture is filtrated, washed with petroleum ether and evaporated. The crude residue is then purified by flash chromatography giving 6.32 g of expected product (67%).
TLC:Rf=0.7 (hexane/EtOAc=50/50).

E. Synthesis of 9-[7,7-difluoro-7-(diethyl phosphinyl)heptyl]-6-chloro-guanine Potassium carbonate (0.83 g, 6 mmoles) is added to a solution of 1-bromo-7,7-difluoro-7-(diethyl-phosphono)hexane (1.05 g, 3 mmoles) and 6-chloro-guanine (0.56 g, 3.3 mmoles) dissolved in 5 ml of anhydrous DMF. The reaction mixture is stirred at 20° C. overnight. DMF is evaporated under reduced pressure. The residue is extracted with ethyl acetate, washed with saturated ammonium chloride and brine, dried over sodium sulfate, filtrated and evaporated, giving 1.63 g of crude which is purified by flash chromatography.
TLC:Rf=0.4 (EtOAc)
960 mg of product are isolated 73%
Rem:19F NMR analysis of the reaction product indicates the presence of another product (±7%). This impurity could not be separated.

F. Synthesis of 9-[7-phosphinyl-7,7-difluoro heptyl]-6-chloro guanine 7 mmoles of trimethylsilyl bromide (0.9 ml) are added to a stirred solution of 2.2 moles (0.95 g) of the product of Part E dissolved in 2.5 ml of anhydrous dichloromethane at 20° C. under argon. Stirring at 20° C. during 4 hours. The crude mixture is kept at 0° C. overnight, evaporated, dissolved in 4.5 ml of acetonitrile and crystallized by addition of 0.7 ml of water. After filtration and evaporation of the residual solvents, the white solid is collected: 475 mg (1.2 mmole), 55% yield. Crystallization of the mother liquors gives another 15% of product.
TLC:Rf=0.2 (eluant: MeOH/EtOAc=1/1).

G. Synthesis of 9-[7-phosphinyl-7,7-difluoroheptyl]guanine 473 mg of the product of Part F (1.2 mmole) are stirred at refluxing temperature in 6.7 ml of 1N HCl overnight. The solution is cooled to 20° C. and neutralized to pH 6-7 by adding triethylammonium bicarbonate pH≃8.5. The white crystals are discarded by filtration and dried under vacuum giving 328 mg of product (75%). This product is recrystallized by dissolution at pH 9 at 110° C. in 8 ml of water + 1 ml of triethylammonium bicarbonate buffer. Addition of a few drops of 1N HCl (at 20° C.) until pH 7. The white precipitate is filtered off and dried under vacuum giving 150 ml of product (35%). Mother liquors contain essentially good product.

EXAMPLE 2

Preparation of 9-(7-phosphinyl-7,7-difluorohept-6-ol)guanine

A. Preparation of 6-benzyloxyhexanol

Pure potassium t-butoxide (50 mmoles, 5.61 g) is added portionwise to a stirred solution of 100 mmoles of hexanediol (11.82 gr) dissolved in 30 ml of THF at room temperature under argon. When addition is complete, 50 mmoles of benzylbromide (5.9 ml) are introduced and the reaction mixture is stirred at room temperature overnight. The white solid is then removed by filtration, the filtrate is evaporated and the residue is dissolved in ethylacetate, washed with saturated ammonium chloride, $H_2O$ and brine. Usual workup and purification by flash chromatography gives finally 7.51 g of product (72%).

B. Preparation of 6-benzyloxyhexanal

DMSO (4.2 ml, 59 mmoles) dissolved in 15 ml of $CH_2Cl_2$ are added to 2.5 ml of oxalylchloride (23 mmoles) dissolved in 27 ml of anhydrous $CH_2Cl_2$ at −78C under argon. After 2 minutes at −78° C., 19 mmoles of 6-benzyl hexanol (3 g) dissolved in 65 ml of anhydrous dichloromethane are slowly added to the reaction mixture which is stirred for 30 minutes at −78° C. and 60 minutes at −35° C. 18.5 ml of triethylamine (139 mmoles) are then added and the reaction mixture is stirred for 2 hours at 20° C. The mixture is quenched by $NH_4Cl$ (saturated aqueous solution), washed 5 times with saturated $NH_4Cl$ and once with brine; after drying over $Na_2SO_4$, filtration and evaporation, the crude product is obtained as an oil which is directly used in the next step withour purification.

C. Preparation of 1-benzyloxy-7,7-difluoro-7-(diethylphosphinyl)heptane-6-ol 26 mmoles of freshly prepared lithium diisopropylamine in 30 cc of THF are slowly added to a stirred solution of difluoromethyl(diethyl)phosphonate (4.9 g, 26 mmoles) at −78° C. under argon dissolved in 28 ml of THF. After 10 minutes at −78° C. the aldehyde from Part B (3.02 g of crude product as obtained by oxidation)dissolved in 28 ml of THF is slowly added to the reaction mixture kept at −78° C. The reaction mixture is stirred at −78° C. for 15 minutes and at 20° C. for 45 minutes. The mixture is quenched by a saturated aqueous $NH_4Cl$ solution, evaporated to dryness; the residue is dissolved in ethyl acetate, washed with saturated $NH_4Cl$, water and brine, dried over $Na_2SO_4$, filtered and evaporated to give 6.94 g of crude mixture which is then purified by flash chromatography giving 3.7 g of pure product (68%).

D. Preparation of Diethyl 7-benzyloxy-1,1-difluoro-2methoxymethvleneoxyheptanphosphonic acid 2.04 moles of methylal (180 ml) and 87 g of diphosphorus pentoxide are successively added to 30 mmoles of product from Part C (11.83 g) dissolved in 180 ml of chloroform and stirred with a mechanical stirrer under a stream of argon. After 30 minutes at 20° C. the crude mixture is poured into an iced, saturated bicarbonate solution. The water suspension is extracted with ethyl acetate. The organic fractions are gathered, washed with brine, dried over $Na_2SO_4$, filtrated, and evaporated, thus giving 9.41 g of product (72%) which is used in the next step without further purification.

E. Preparation of Diethyl 1,1-difluoro-7-hydroxy-2methoxymethyleneoxyheptanphosphonic acid 8.6 mmoles (1.35 g) of commercially available Pd on carbon are added to a solution of product from Part D dissolved in 310 ml of anhydrous THF and the mixture is stirred under $H_2$ at atmospheric pressure overnight. (461 ml of hydrogen are consumed). The mixture is filtrated over celite and evaporated, giving 6.28 g of product (88%) used in the next step without further purification.

F. Preparation of 6-chloro-9-(7-diethylphosphinyl-7,7-difluoro-6-methyloxymethyleneoxyheptyl)guanine 28 mmoles of potassium carbonate (anhydrous) (3.87 g) are added on one portion to a stirred solution of product from Part E (14 mmoles, 5.77 g) and 6-chloroguanine (15.5 mmoles, 2.61 g) at 20° C. under argon. The reaction mixture is stirred at 20° C. overnight and evaporated to dryness. The residue is dissolved in ethyl acetate, washed with aqueous $NH_4Cl$ solution (4×) and brine, dried over $Na_2SO_4$, filtered and evaporated giving 7 g of crude product which is purified by flash chromatography and finally 10.8 mmoles of expected product are isolated (77%).

G. Preparation of 9-(7-phosphinyl-7,7-difluorohept-6ol)guanine 8 mmoles of TMSBr (1.05 ml) are 153 to a stirred solution of product of Part F (2 mmoles, 7 g) dissolved in 2 ml of anhydrous dichloromethane at 20° C. under argon. After 4 hours at 20° C. the reaction mixture is evaporated to dryness and the residue is dissolved in 2.5 ml of acetonitrile; a few drops of water are added and an oil is separated out of the solution. This oil is dissolved in 9 ml of 1N HCl and stirred at refluxing temperature during 6 hours. The reaction mixture is evaporated to dryness and traces of water are eliminated by 2 successive evaporations of isopropanol. The residue is dissolved in ethanol, filtrated and treated with a few drops of deoxylene oxide—a white solid is precipitated and purified by a sephadex column giving the final product in 30% yield.

EXAMPLE 3

Preparation of 9-(7-phosphono-7,7-difluoroheptyl) guanine, ethyl ester 3 gr (7 mmoles) of 9-[7,7-difluoro-7-(diethylphosphinyl)heptyl]-6-chloroguanine (prepared according to Example 1, procedure E) are dissolved in 30 ml of 1N aqueous HCl and 4 ml of THF. The reaction mixture is heated at 90°–100° C. for 15 hours, cooled to 20° C., and evaporated to dryness. The residue is dried by 3 succesive evaporations of 50 ml of isopropanol, then dissolved in hot ethanol and crystallized on cooling. The solid fraction is dissolved in ethanol and precipitated by addition of propylene oxide; the precipitate is crystalized again from ethanol to give 1.3 gr of the desired 9-(7-phosphono-7,7-difluoroheptyl)guanine, monoethyl ester. The mother liquors contain essentially 9-(7-phosphono-7,7-difluoroheptyl)guanine, diethyl phosphonic ester.

TLC:Rf=0.3 (MeOH/EtOAc=40/60) sprayed with $MoO_3/H_2SO_4$; visible in UV m.p.: 185°–187° C.

EXAMPLE 4

Preparation of 9-(6-phosphono-6-fluoroheptyl)guanine

A. Synthesis of 6-O-benzylhexanal 22.4 ml of DMSO dissolved in 70 ml of dichloromethane are slowly added to a solution of 13.5 ml of oxalyl chloride dissolved in 145 ml of anhydrous dichloromethane at −78° C. under argon. The reaction mixture is stirred at −78° C. for 2 to 3 minutes and 15.86 gr (76 mmoles) of 6-O-benzyl-hexane-1ol dissolved in 145 ml of dichloromethane are added slowly. The reaction mixture is stirred at −35° C. for 2½ hours and 97 ml of triethylamine are added. The mixture is stirred at −35° C. for 10 minutes and at 20° C. for 1 hour, washed with saturated aqueous ammonium chloride and brine, dried over $Na_2SO_4$, filtered and evaporated to give 33 gr of crude product which is purified by flash chromatography on silica gel to give 7.65 gr of product (43%).

B. Synthesis of 6-O-benzyl-benzyl-1-(diethyl-phosphinyl)hexane-1-ol 5.4 ml of diethylphosphite dissolved in 15 ml of anhydrous THF are slowly added to a suspension of sodium hydride (2 gr of a suspension at 50% in oil) in 60 ml of THF. The reaction mixture is stirred for 15 min (time required to observe completion of gas evolution) at 25° C. and 7.19 gr (34.6 mmoles) of 6-benzylhexanal in 50 ml of THF are added to the reaction mixture which is stirred at 20° C. for 15 hours, quenched with aqueous saturated ammonium chloride and evaporated to dryness. The residue is extracted with ethyl acetate, washed with brine, dried over $Na_2SO_4$, filtered and evaporated to give 8.77 g of a crude product which is used without further purification in the next step.

C. Synthesis of 6-O-benzyl-benzyl-1-flouro-1-(diethylphosphinyl)hexane 28 mmoles of diethylaminosulfur trifluoride, DAST (3.5 ml) are slowly added to a stirred solution of 23 mmoles (7.8 gr) of 6-O-benzyl-1-hydroxy-1-(diethylphosphinyl)hexane dissolved in 70 ml of $CH_2Cl_2$ at $-78°$ C. The mixture is stirred at -78° C. The mixture is stirred at $-78°$ C. for 20 minutes and at 20° C, for 2 hours, quenched at 0° C. with 15 cc of methanol, evaporated to dryness and purified by flash chromatography on silica gel to give 1.6 gr of expected product (21%).

The final product is then prepared in a manner analagous to that described in Example 1 beginning at Part C.

EXAMPLE 5

Tablets are prepared each having the composition

| | |
|---|---|
| 9-(7-phosphinyl-7,7-difluoroheptyl)guanine | 5 mg |
| starch | 45 mg |
| lactose | 48 mg |
| magnesium stearate | 2 mg |

The granulation obtained upon mixing the lactose with active compound and the starch is dried, screened and mixed with the stearate. The mixture is then compressed to give a tablet.

EXAMPLE 6

Hard gelatin capsules are prepared each having the composition

| | |
|---|---|
| 9-(7-phosphinyl-7,7-difluorohept-6-ol)guanine | 5 mg |
| talc | 5 mg |
| lactose | 90 mg |

The formulation is prepared by passing the dry powders of active compound talc and lactose through a fine mesh screen and mixing well. The powder is then filled into hard gelatin capsules.

EXAMPLE 7

Ampules containing 1 ml of the following composition are prepared for injectable suspensions.

| | Weight % |
|---|---|
| 9-(7-phosphono-7,7-difluoroheptyl)guanine ethyl ester | 0.5 |
| polyvinylpyrrolidone | 0.5 |
| lecithin | 0.25 |
| sterile water to make | 100.00 |

The materials are mixed, homogenized, and filled into a 1 ml ampule which is sealed and autoclaved 20 minutes at 120° C. Each ampule contains 5 mg per ml of the active compound

EXAMPLE 8

9-(5-phosphono-5,5-difluoropentyl)guanine

A. Preparation of 1-iodo-5,5-difluoro-5-(diethylphosphenyl)pentane n-Butyllithium (33 moles, 18.8 ml of a 1.75M solution in hexane) is added dropwise to a stirred solution of diisopropylamine (33 mmoles, 3.34 g) in 40 cc of anhydrous THF (40 ml) at 0° C. under argon. The LDA solution is cooled to $-70°$ C. and difluoromethyl-0,0-diethylphosphonate (30 mmoles, 5.64 g) in of THF (20 ml) is added via a syringe. After 30 min. at $-78°$ C., the solution is slowly transferred via a short needle to a stirred cooled ($-78°$ C.) solution of 1,3-diiodobutane (30 mmoles, 9.3 g) dissolved in 30 cc of anhydrous THF with argon. The reaction mixture is stirred at $-78°$ C. for 3 hours. The temperature is slowly raised up to 20° C. and the mixture is quenched with excess saturated ammonium chloride and evaporated to dryness. The residue is suspended in ethyl acetate, washed with water and brine, dried over sodium sulfate, filtrated, evaporated and purified by flash chromatography on silica gel giving 10 mmoles (3.7 g) of expected product (33% yield).

B. Preparation of 9-[5,5-difluoro-5-(diethylphosphinyl)pentyl]-6-chloroguanine.

The title compound was prepared in a manner analagous to that of Example 1E.

C. Preparation of 9-(5-phosphono-5,5-difluoropentyl)guanine)

The title compound was prepared in a manner analogous to that of Example s 1F and 1G

We claim:

1. A compound of the formula

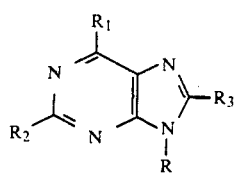

wherein R is a phosphoroalkyl group of the formula:

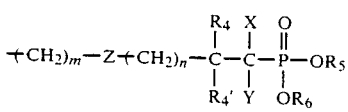

wherein m and n are each an integer of from 1 to 5 with the proviso that m+n must be an interger of from 2 to 6;

Z is an oxy group or a methylene group;
R₄ is a hydrogen and R₄' is a hydrogen or hydroxy group or R₄ and R₄' taken together with the carbon atom to which they are attached form a keto group;
X and Y are each a hydrogen, fluoro or chloro group with the proviso that both of X and Y cannot be hydrogen;
$R_5$ and $R_6$ are each a hydrogen or a $(C_1-C_4)$alkyl group;
$R_1$ is a hydroxy or sulfhydryl group;
$R_2$ is a hydrogen or amino group; and
$R_3$ is a hydrogen, amino, hydroxy or —NH—NH₂ group;
or a pharmaceutically acceptable salt thereof.

2. A compound of claim 1 wherein $R_2$ is an amino group.

3. A compound of one of claims 1 or 2 wherein one or both of X and Y are fluoro groups.

4. A compound of one of claims 1 or 2 wherein $R_3$ is an amino group.

5. A compound of one of claims 1 or 2 wherein Z is a methylene and wherein n + m is an integer of from 2 to 5.

6. A compound of claim 1 which is 9-(7-phosphono-7,7difluoroheptyl)guanine.

7. A compound of claim 1 which is 9-(7-phosphono-7,7-difluorohept-6-ol)guanine.

8. A compound of claim 1 which is 9-(7-phosphono-7,7-difluoroheptyl)guanine ethyl ester.

9. A compound of claim 1 which is 9-(6-phosphono-6-fluoroheptyl)guanine.

10. A compound of claim 1 which is [9-(5-phosphono-5,5-difluoropentyl)guanine].

11. A compound of claim 1 which is 8-amino-[9-(5-phosphono-5,5-difluoropentyl)]guanine.

12. A method of suppressing the immune system in a patient in need thereof which comprises administering to the patient an effective amount of a compound of the formula

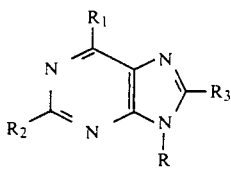

wherein R is a phosphonoalkyl group of the formula:

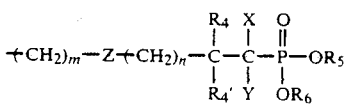

wherein
m and n are each an integer of from 1 to 5 with the proviso that m + n must be an integer of from 2 to 6;
Z is an oxy group or a methylene group;
R₄ is a hydrogen and R₄' is a hydrogen or hydroxy group or R₄ and R₄' taken together with the carbon atom to which they are attached form a keto group;
X and Y are each a hydrogen, fluoro or chloro group with the proviso that both of X and Y cannot be hydrogen;
$R_1$ is a hydroxy or sulfhydryl group;
$R_2$ is a hydrogen or amino group; and
$R_3$ is a hydrogen, amino, hydroxy or —NH—NH₂ group;
or a pharmaceutically acceptable salt thereof.

13. A method of claim 12 wherein $R_2$ is an amino group.

14. A method of one of claims 12 or 13 wherein one or both of X and Y are fluoro groups.

15. A method of one of claims 12 or 13 wherein $R_3$ is an amino group.

16. A method of one of claims 12 or 13 wherein Z is a methylene and wherein n+m is an integer of from 3 to 5.

17. A method of claim 12 wherein the compound is 9-(7-phosphono-7,7-difluoroheptyl)guanine.

18. A method of claim 12 wherein the compound is 9-(7-ohosphone-7,7-difluorohept-6-ol)guanine.

19. A method of claim 12 wherein the compound is 9-(7-phosphono-7,7-difluoroheptyl)guanine ethyl ester.

20. A method of claim 12 wherein the compound is 9-(6-phosphono-6-fluoroheptyl)guanine.

21. A method of claim 12 wherein the compound is [9-(5-phosphono-5,5-difluoropentyl)guanine].

22. A method of claim 12 wherein the compound is 8-amino-[9-(5-phosphono-5,5-difluoropentyl)]guanine.

23. A method of inhibiting purine nucleoside phosphorylase in a patient in need thereof which comprises administering to the patient an effective amount of a compound of the formula:

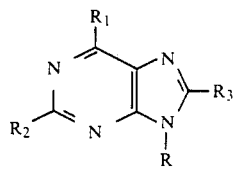

wherein R is a phosphonoalkyl group of the formula

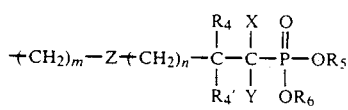

wherein m and n are each an integer of from 1 to 5 with the proviso that m+n must be an integer of from 2 to 6;
Z is an oxy group or a methylene group;
R₄ is a hydrogen and R₄' is a hydrogen or hydroxy group or R₄ and R₄' taken together with the carbon atom to which they are attached form a keto group;
X and Y are each a hydrogen, fluoro or chloro group with the proviso that both of X and Y cannot be hydrogen;
$R_5$ and $R_6$ are each a hydrogen or $(C_1—C_4)$alkyl group;
$R_1$ is a hydroxy or sulfhydryl group;
$R_2$ is a hydrogen or amino group; and
$R_3$ is a hydrogen, amino, hydroxy or—NH—NH₂ group; or a pharmaceutically acceptable salt thereof.

24. A method of claim 23 wherein $R_2$ is an amino group.

25. A method of one of claims 23 or 24 wherein one or both of X and Y are fluoro groups.

26. A method of one of claims 23 or 24 wherein $R_3$ is an amino group.

27. A method of one of claims 23 or 24 wherein Z is a methylene and wherein n+m is an integer of from 2 to 5.

28. A method of claim 23 wherein the compound is 9-(7-phosphono-7,7-difluoroheptyl)guanine.

29. A method of claim 23 wherein the compound is 9-(7-phosphono-7,7-difluorohept-6-ol)guanine.

30. A method of claim 23 wherein the compound is 9-(7- phosphono-7,7-difluoroheptyl)guanine ethyl ester.

31. A method of claim 23 wherein the compound is 9-(6-phosphono-6-fluoroheptyl)guanine.

* * * * *

UNITED STATES PATENT AND TRADEMARK OFFICE
CERTIFICATE OF CORRECTION

PATENT NO. : 4,988,680

DATED : January 29, 1991

INVENTOR(S) : Serge J. Halazy, et al.

It is certified that error appears in the above-identified patent and that said Letters Patent is hereby corrected as shown below:

At Column 1, line 33, patent reads "suppresion" and should read --suppression--.

At Column 2, line 4, patent reads "$(C_{\_}-C_4)$" and should read --$(C_1-C_4)$--.

At Column 3, line 33, patent reads "8-amino-[9-(5-phosphono-5,5-difluoropentyl) guanine]" and should read --[9-(5-phosphono-5,5-difluoropentyl)] guanine--.

At Column 8, line 10, patent reads "$B_zO-(CH_2)_m-CH_2-(CH_2)_n-CHO$" and should read --$B_zO-(CH_2)_m-CH_2-(CH_2)_n-CHO$     10--.

At Column 9, line 60, patent reads "*Telosporea* the" and should read --*Telosporea* of the--.

At Column 13, line 38, patent reads "Rf= =0.35" and should read --Rf = 0.35--.

At Column 15, line 38, patent reads "-2methoxymethvleneoxyheptanphosphonic" and should read ---2-methoxymethyleneoxyheptanphosphonic--.

At Column 15, line 54, patent reads "-2methoxymethyleneoxyheptanphosphonic" and should read ---2-methoxymethyleneoxyheptanphosphonic--.

At Column 16, line 12, patent reads "-6ol" and should read ---6-ol--.

At Column 16, line 13, patent reads "are 153" and should read --are added--.

At Column 16, line 60, patent reads "-1o1" and should read ---1-o1--.

At Column 17, line 2, patent reads "benzyl-benzyl-1" and should read --benzyl-1--.

UNITED STATES PATENT AND TRADEMARK OFFICE
CERTIFICATE OF CORRECTION

PATENT NO. : 4,988,680

DATED : January 29, 1991

INVENTOR(S) : Serge J. Halazy, et al.

It is certified that error appears in the above-identified patent and that said Letters Patent is hereby corrected as shown below:

At Column 17, line 9, patent reads "6-benzyl" and should read --6-O-benzyl--.

At Column 17, line 19, patent reads "6-O-benzyl-benzyl-1" and should read --6-O-benzyl-1--.

At Column 18, line 59, patent reads "phosphoroalkyl" and should read --phosphonoalkyl--.

At Column 19, line 25, patent reads "7,7difluoro" and should read --7,7-difluoro--.

At Column 20, line 16, patent reads "(7-ohosphone-" and should read --(7-phosphono---.

Signed and Sealed this

Twelfth Day of January, 1993

Attest:

DOUGLAS B. COMER

*Attesting Officer*     Acting Commissioner of Patents and Trademarks